(12) United States Patent
Russell et al.

(10) Patent No.: US 8,632,269 B2
(45) Date of Patent: Jan. 21, 2014

(54) ORAL CARE INSTRUMENT INCLUDING AN ORAL CARE AGENT

(71) Applicants: Colgate-Palmolive Company, New York, NY (US); Barbara Canady, Princeton, NJ (US)

(72) Inventors: Bruce M. Russell, Howell, NJ (US); Van Canady, Princeton, NJ (US); Steven M. Sorrel, Millwood, NY (US); Candi Rancel, Stamford, CT (US); Heng Cai, Skillman, NJ (US); Douglas J. Hohlbein, Hopewell, NJ (US); Eduardo J. Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/765,575

(22) Filed: Feb. 12, 2013

(65) Prior Publication Data
US 2013/0149663 A1   Jun. 13, 2013

Related U.S. Application Data

(60) Continuation of application No. 13/309,135, filed on Dec. 1, 2011, now Pat. No. 8,376,643, which is a division of application No. 12/037,278, filed on Feb. 26, 2008, now Pat. No. 8,092,110, which is a continuation of application No. PCT/US2006/033021, filed on Aug. 24, 2006.

(60) Provisional application No. 60/711,577, filed on Aug. 26, 2005.

(51) Int. Cl.
*B43K 5/12* (2006.01)

(52) U.S. Cl.
USPC .............. 401/194; 401/47; 401/270; 401/282

(58) Field of Classification Search
USPC ......... 401/183–186, 270, 277, 278, 279, 286, 401/288, 132–135, 282, 284, 285, 28, 47, 401/194; D4/14, 110–112
See application file for complete search history.

(56) References Cited

U.S. PATENT DOCUMENTS

| 1,673,638 A | 6/1928 | Peterson |
| 1,925,818 A | 9/1933 | Primeau et al. |

(Continued)

FOREIGN PATENT DOCUMENTS

| CN | 1046272 | 10/1990 |
| DE | 10153863 | 5/2003 |

(Continued)

OTHER PUBLICATIONS

International Search Report and Written Opinion in International Application No. PCT/US06/033021, mailed Dec. 18, 2006.

*Primary Examiner* — David Walczak
(74) *Attorney, Agent, or Firm* — Ryan M. Flandro

(57) ABSTRACT

An oral care instrument includes at least one oral care agent. In one embodiment, the oral care agent can be provided on one or more surfaces of the oral care instrument or included within cavities within the head or in one or more surfaces of a head. In other embodiment, the oral care agent can be provided in or on a thin slab subsequently bonded onto a surface, or applied as a stable coating. The oral care instrument can also be provided with a wear indicator. The oral care agents can be released during one use, during multiple uses, or throughout the life of the instrument. Water, oral secretions and/or chemicals within the mouth can activate the oral care agents.

18 Claims, 7 Drawing Sheets

(56) References Cited

U.S. PATENT DOCUMENTS

| | | | |
|---|---|---|---|
| 1,987,849 A | 1/1935 | Hanschke | |
| 1,995,374 A | * 3/1935 | Young | 401/268 |
| 3,378,870 A | 4/1968 | Matsunaga | |
| 3,491,396 A | 1/1970 | Eannarino et al. | |
| 3,542,519 A | 11/1970 | Montalto et al. | |
| 4,802,255 A | 2/1989 | Breuer et al. | |
| 5,061,106 A | 10/1991 | Kent | |
| 5,340,581 A | 8/1994 | Tseng et al. | |
| 5,723,132 A | 3/1998 | Tseng et al. | |
| D402,470 S | 12/1998 | Jeannet et al. | |
| 5,906,834 A | 5/1999 | Tseng | |
| D414,340 S | 9/1999 | Jeannet et al. | |
| D414,609 S | 10/1999 | Jeannet et al. | |
| 5,998,431 A | 12/1999 | Tseng et al. | |
| 6,024,012 A | 2/2000 | Luzenberg, Jr. | |
| 6,085,379 A | 7/2000 | Stafford | |
| 6,108,847 A | 8/2000 | Cueman et al. | |

FOREIGN PATENT DOCUMENTS

| | | |
|---|---|---|
| DE | 10241283 | 3/2004 |
| GB | 880228 | 10/1961 |
| GB | 2403896 | 1/2005 |
| RU | 2055507 | 3/1996 |
| WO | WO 90/08488 | 8/1990 |
| WO | WO 99/47020 | 9/1999 |
| WO | WO 2004/021914 | 3/2004 |
| WO | WO 2005/010624 | 2/2005 |
| WO | WO 2005/092145 | 10/2005 |
| WO | WO 2006/020700 | 2/2006 |

* cited by examiner

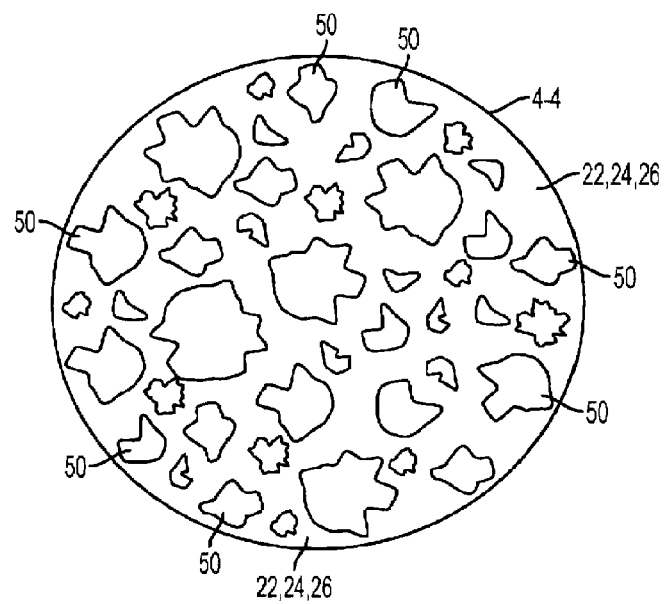
FIG. 4
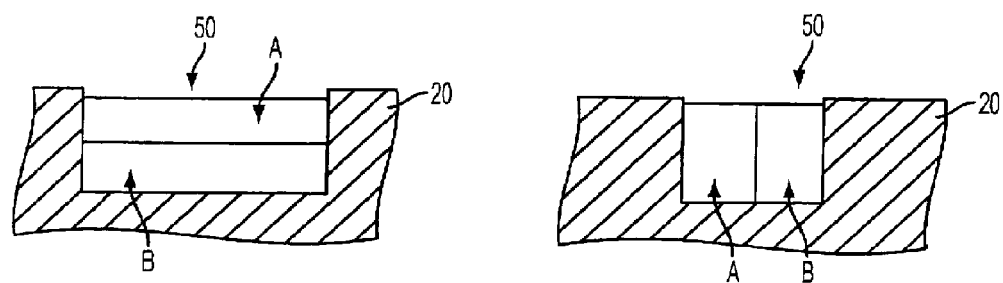
FIG. 5
FIG. 6

ORAL CARE INSTRUMENT INCLUDING AN ORAL CARE AGENT

CROSS-REFERENCE TO RELATED APPLICATIONS

The present application is a continuation of U.S. application Ser. No. 13/309,135, filed on Dec. 1, 2011, now U.S. Pat. No. 8,376,641, which is a divisional of U.S. application Ser. No. 12/037,278, filed on Feb. 26, 2008, now U.S. Pat. No. 8,092,110, which is a continuation of International Application Serial No. PCT/US2006/033021, filed on Aug. 24, 2006, which further claims the benefit of U.S. Provisional Application Ser. No. 60/711,577, filed on Aug. 26, 2005, the entireties of which are herein incorporated by reference.

FIELD OF THE INVENTION

The present invention relates to an oral care instrument with at least one oral care agent that can be delivered within, the mouth of a user to provide the user with enhanced oral heath. The present invention also pertains to such an oral care instrument including a wear indicator that informs the user when the oral care agent has been depleted.

BACKGROUND OF THE INVENTION

People exhibit many forms of poor oral health including tooth decay, periodontal diseases and bad breath (halitosis). Tooth decay and periodontal disease are typically caused by harmful bacteria within the mouth. When the harmful bacteria mixes with proteins present in saliva, a film of plaque is formed on the teeth and soft tissue. If the plaque is not removed, it can attack the teeth and create cavities. Additionally, the plaque will attack the soft tissue within the mouth and cause gum disease, the leading cause of tooth loss in adults. As a result, decreasing the amount of harmful bacteria in the mouth has long been the target of persons working in the oral health care field.

The most common way of minimizing the harmful bacteria within the mouth is brushing with a dentifrice that delivers at least one oral care agent into the mouth. Orally introduced liquids, including oral rinses, are also utilized to provide additional oral care beyond that achieved while brushing. Mouthwashes may also be used to deliver breath freshening agents within the mouth in an attempt to eliminate bad breath.

Unfortunately, people do not always have the time to provide themselves with adequate oral care. For example, a busy person may not have the time or patience to brush thoroughly, floss and/or use an oral rinse. Alternatively, certain people may consider anything more than brushing their teeth to be unnecessary. For either reason, these people may leave a significant amount of harmful bacteria within their mouths after completing their oral care routines, which can begin to attack the teeth and gums.

Additionally, even when all available and recommended products are used, they may not be as effective as they could be if delivered simultaneously. For example, using a dentifrice and an oral rinse at different times may diminish any synergistic effect that they could provide to the user when used simultaneously.

BRIEF SUMMARY OF THE INVENTION

An aspect of the present invention pertains to an oral care instrument that includes and delivers an oral care agent within the mouth of a user. The oral care instrument includes a head having at least a portion formed of a material that defines cavities. At least one oral care agent is provided in a plurality of the cavities and dispensed within the mouth of a user when the oral care agent(s) contact a fluid or chemical within the oral cavity. In another aspect of the present invention, the oral care instrument includes a wear indicator for indicating the amount of oral care agent.

Another aspect of the present invention relates to an oral care device formed of a polymer that receives at least one oral care agent. The oral care agent(s) can be included in or on one or more surfaces of the oral care instrument for delivery into the oral cavity. The oral care agent(s) can be contained, within cavities in one or more surfaces of a head. Alternatively, the oral care agent(s) can be formed into, or carried by, a thin slab subsequently bonded onto the toothbrush head; or applied onto the toothbrush head as a stable coating. The oral care agents can be released during one use, during multiple uses, or throughout the life of the instrument. Water, oral secretions and/or chemicals within the mouth can activate the oral care agents.

BRIEF DESCRIPTION OF THE FIGURES

FIG. 4 is an enlarged portion 4-4 of the surface of the instrument of FIGS. 1-3;

FIG. 5 is a cross section of one embodiment of a cavity shown in FIG. 4;

FIG. 6 is a cross section of one embodiment of a cavity shown in FIG. 4;

DETAILED DESCRIPTION OF THE INVENTION

Figure 1:
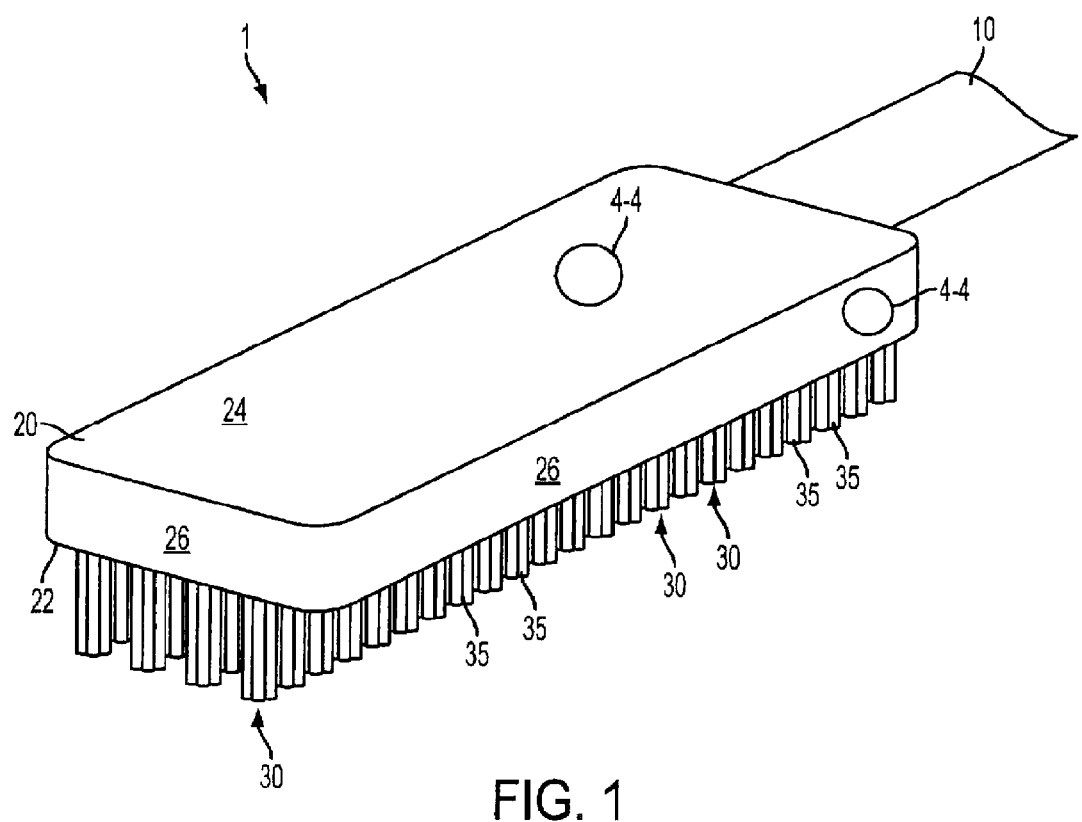
FIG. 1 is an isometric view of an oral care instrument according to aspects of the present invention.

FIG. 1 illustrates one embodiment of an oral care instrument 1 having an elongated handle 10 and a head 20 intended to be introduced into the mouth or oral cavity of a user. The oral care instrument 1 is not limited to a toothbrush as shown and described, but can have any shape or structure and perform any function that permits it to deliver oral care agents to the user, with non-limiting examples of other oral care instruments including tongue cleaners and portable brush, toothpick combinations. The instrument 1 can be used once and then discarded, or it can be used repeatedly over a period of time. The elongated handle 10 may be formed of many different shapes and with a variety of constructions that permit the oral care instrument 1 to be readily gripped and manipulated within the mouth of the user.

Figure 2:
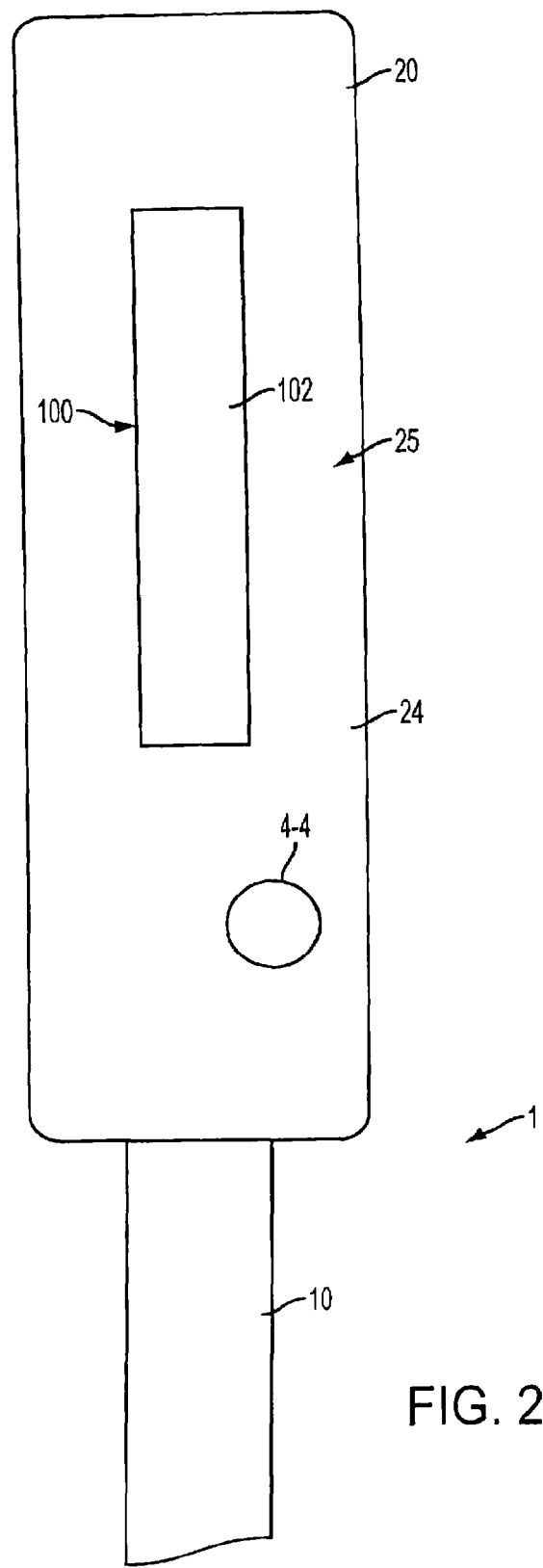
FIG. 2 is a view of one surface of the instrument of FIG. 1.
Figure 3:
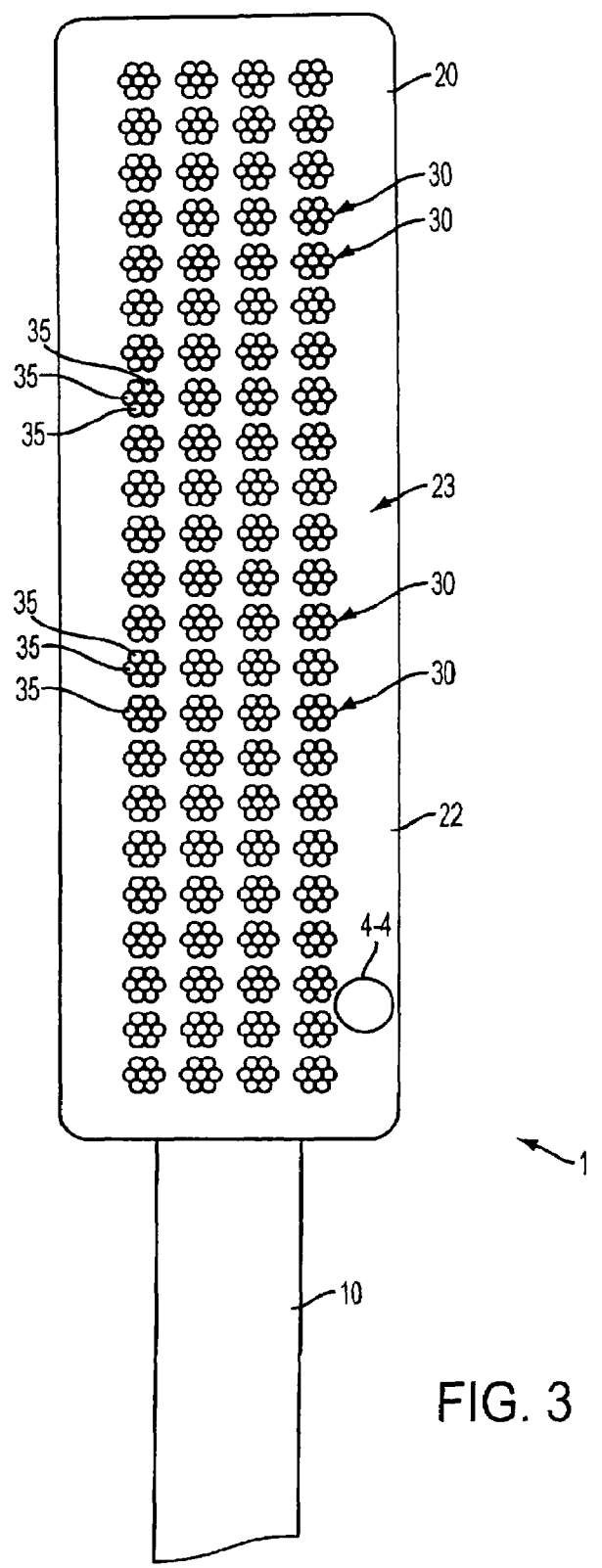
FIG. 3 illustrates a surface of the instrument of FIG. 1 taken opposite FIG. 2.

The head 20 includes multiple surfaces that are exposed to fluids within the mouth during use. In the embodiment illustrated in FIGS. 1-3, the head 20 includes a first surface 22 on a first side 23 and a second surface 24 on a second, opposite side 25. Sidewalls 26 extend between the surfaces 22, 24. Oral care elements 30 can extend from either or both surfaces 22, 24 of the head 20, which elements 30 can include teeth cleaning elements 35, such as elongated bristles or elastomeric fingers, or soft tissue cleaning elements such as tongue cleaning members (not shown) extending from either surface 22, 24. A third example includes a head 20 having teeth cleaning elements 35 extending from the first surface 22 and tongue cleaning elements (not shown) extending from the second surface 24.

The oral care elements 30 disclosed herein are not limited to those discussed above. Instead, the term "oral care element" is generic and intended to include all types of elements that can be used within a mouth including different tooth and soft tissue cleaning members that are not mentioned above, gum massaging members and other forms of oral cleaning or massaging members.

Regardless of the number or position of the oral care elements 30 provided on the head 20, the head 20 also includes at least one oral care agent for introducing, into the mouth to perform an intended function. In an embodiment, the oral care agent(s) can be provided in cavities 50 (See FIG. 4) formed or present in the head 20. The oral care agent(s) can also be included in or on a separate member 100 positioned on one or more of the surfaces 22, 24 or 26 of the head 20 (See FIG. 2). This member 100 may be provided in place of or in addition to, the cavities 50 within the head 20.

The head 20 is generally formed of a material having a plurality of the externally exposed cavities 50 that are open to their respective outer surface 22, 24, 26. The entire head 20 can be formed of this material or the material can be applied over an inner core (not shown). The material used to form the head 20 can include any one of a wide variety of commercially available polymers, such as a thermoplastic polymer for example. In an embodiment, the oral care instrument 1 is formed from a polypropylene, such that upon manufacture it is formed with internally extending cavities. Different thermoplastic polymers or polymers having different molecular weights typically have different melting and solidifying characteristics. Therefore, it is within the purview of a skilled artisan to select a polymer suitable for a given application. The oral care instrument 1 can be formed of polypropylene materials such as those available from M.A. Industries, in an embodiment, the head 20 formed of a polypropylene material is manufactured using a sintering process. The head 20 can formed at the same time as the remaining portions of the oral care instrument 1 as a single, continuous member. Alternatively, the head 20 can be manufactured as a component that is assembled as part of the instrument 1. The head 20 can then be attached through a number of techniques including welding via ultrasonics, heat staking, laser, etc. or through mechanical methods that also permit the head 20 to be removed and discarded.

As used herein, the term "cavity" is intended to refer to an opening in the head 20, whether present in the head material itself or intentionally formed therein, that preferably does not extend all the way through the head. As used herein, the term "exposed surface" relates to a surface that defines the shape of the head 20 and which generally defines the boundary between the head 20 and its environment. The externally exposed cavities 50 are capable of receiving and retaining one or more of the dispensable oral care agents. The cavities 50 can receive these agents in a powered form, a liquid form or both. In an embodiment, the cavities 50 will receive and retain the oral care agent(s) until a predetermined amount has been received or the cavity is filled. The size and shape of these cavities 50 may be varied so they can include greater amounts of an oral care agent or an oral care agent with larger or different shaped molecules.

It is understood that a wide variety of material specifications (such as polymer type, polymer size, granule size distribution, the type of oral care agent used, oral care agent particle size distribution and ratio of porous polymer to oral care agent) and also a wide variety of manufacturing/processing parameters (such as temperature and pressure) may be used to provide an instrument 1 having various advantageous characteristics including cavity sizing, shape and spacing. For example, the oral care instrument 1 can have cavities 50 that deliver oral care agent(s) into the mouth of a user at different rates. These rates can be controlled, for example, by the size of the exposed surface area of the respective cavity 50 and contained oral care agent in the outer surface 22, 24, 26 of the head, the shape of the cavities 50, the depth of the cavities 50 and/or the characteristics of the contained oral care agent(s).

Adjacent cavities 50 can have different sizes in order to accommodate different amounts of oral care agent(s) or different molecular sized oral care agent(s). As a result, the oral care instrument 1 can have different oral care agent release characteristics that control when and how much of each oral care agent is delivered into the oral cavity. For example, in art embodiment in which it is desired that the oral care agent(s) be released relatively quickly from the oral care instrument 1, a larger thermoplastic granule size for the head 20 may preferably be selected and, where it is desired that the oral care agent(s) be dispensed more slowly, a smaller thermoplastic granule size may preferably be selected.

Adjacent cavities 50 within the outer surfaces of the head 20 can carry the same or different oral care agents. Similarly, the same void 50 can carry different oral care agents (A, B), either layered on top of each other (FIG. 5) for controlled release timing or adjacent to each other (FIG. 6) so they will react simultaneously when they come into contact with an activator.

The active oral care agents can function as, for example, abrasives, mouth fresheners, tooth whiteners, vitamins, anti-bacterial/anti-microbial agents, plaque dispersants, de-sensitizing agents for the mouth and teeth, anti-cavity agents, and/or combinations of these functional agents to provide individual or combined, synergistic benefits. Oral care agents can also include flavorings, decorations, nutritional and body supplements such as calcium. The calcium could, for example, be provided in 1 mg single use dosages. The flavorings could be released to indicate that the oral care element 1 is functioning properly or to indicate that the instrument 1 is exhausted and ready to be disposed or recharged. Also, the oral care agents could eliminate particular enzymes from within the mouth of the user. The decorations applied by the oral care agents could temporarily add coloring, sparkle, glitter and/or indicia to the teeth of the user. Further, the lack of fluid within the mouth could trigger an oral care agent, such as stimulant for the salivary gland, provided within the cavities 50. The amount and rate of delivery for these agents will depend on the amount needed and the agent being applied.

During the production of the oral care instrument 1, the oral care agents can be delivered to the cavities in a solid and/or liquid compound. In one embodiment, the material of the oral care instrument 1 is immersed in a desired liquid so that the oral care agent(s) within the liquid can flow and remain within the cavities 50. As it dries, the oral care agent A, B becomes secure within the cavities 50. It is also possible to impregnate the cavities 50 of the portion of the head 20 with desired oral care agent(s) during production it is also understood that a spent oral care instrument, i.e., one in which the oral care agent(s) has been depleted, may advantageously be recharged with an oral care agent by immersing it again in a liquid that carries the desired oral care agent(s). The cavities 50 can be replenished (recharged) on a regular basis, including daily for those instruments providing single dosages of at least one oral care agent.

Once the cavities 50 receive their intended oral care agent(s), the head 20 may be advantageously used to dispense or release the oral care agent(s) within the mouth. The oral care agents will typically leach from their respective cavities 50 when they come into contact with fluids and/or chemicals within the mouth. According to an aspect of the present invention, active oral care agents that have been impregnated in the head material, for example, can be released into the mouth while brushing one's teeth. During the tooth brushing process water and chemicals present in the mouth of a user will come into contact with the oral care agent(s) within the cavities 50 in the head 20. This will create a reaction in which the impregnated oral care agent(s) will leach out from the cavities 50 within the head 20. Additionally, the use of different oral care agents in cavities 50 of the same head 20 has the capability of providing a synergistic benefit to the user. This can be especially useful when there are two beneficial oral care agent(s) which, in ideal circumstances, should be kept separated from each other until the desired time of use. In this manner the oral care instrument 1 can deliver multiple benefits to the user at one time.

The oral care instrument 1 is also able to deliver the benefits of a dentifrice by impregnating the head material with the chemicals and abrasives found in toothpaste, for example. In such an embodiment, it would be possible to deliver some of the chemical and mechanical benefits of toothpaste solely through use of the toothbrush without toothpaste being applied to the cleaning elements of the toothbrush. At least one of the dispensed oral care agents could also operate as a catalyst or enhancer for the toothpaste or other agents introduced into the mouth. Also, with this oral care instrument 1, it may be possible to deliver the benefits of a chemical, such as chlorhexidine for example, in a more efficacious manner.

The delivery member 100 discussed above can provide or include the oral care agents discussed above and also function as a wear indicator. This member 100 can be located at any position on the head 20 and can provide notice to the user when the oral care agent is depleted. In certain embodiments, the member 100 may visually communicate the existence of the at least one oral care agent. In a non-limiting illustrative embodiment, the delivery member 100 is shown as a strip 102 on the second surface 24. The delivery member 100 can have any shape and be located on or in any surface(s) on the instrument 1 that can be viewed by the user. In addition to identifying when the instrument 1 needs to be discarded or recharged, the delivery member 100 can also include and deliver at least one of the above-discussed oral care agents within the oral cavity.

In an embodiment, the delivery member 100 is removable and one or more replacement strips 102 can be applied in its place, in series or in parallel, to perform the same function(s) as the delivery member 100. These replacement strips 102 can be applied after each use of the instrument 1 or after repeated uses. Single or multiple strips can also be applied on a head surface to deliver multiple individual benefits or benefits that arise from the combined presence of multiple different strip actives. Such strips could be sold separately and applied by a user as desired. For the user's convenience, the replacement strips 102 could be carried within a recess or compartment in the handle 10 of the instrument 1.

Replacement/enhancement strips 102 that perform different functions within the mouth can also be provided. For example, the replacement/enhancement strips 102 can be designed to freshen breath, activate salivary glands, and/or de-sensitize teeth, etc. In such embodiments, these different functioning strips 102 can be applied to the instrument 1 in place of, or in addition to, the strips 102 that are regularly used on the head 20 to kill harmful bacteria within the mouth, for example.

Figure 7:
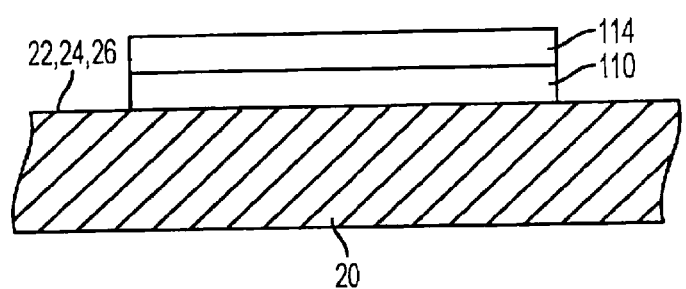
FIG. 7 is a partial cross section of the instrument of FIG. 2.
Figure 8:
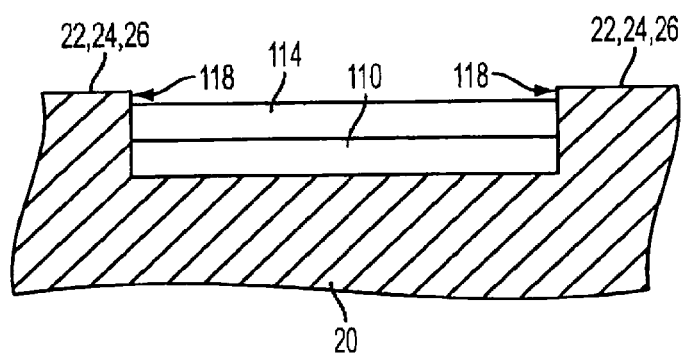
FIG. 8 is a partial cross section of an instrument according to an alternative embodiment of the present invention.

As illustrated in the embodiment of FIG. 7, the delivery member 100 (and replacement strips 102, see FIG. 2) includes a first layer 110 preferably of a water insoluble material, such as a resin, that can hold the oral care agent(s) being delivered within the mouth. The water insoluble material maintains the structure of the delivery member 100 as the oral care agent leaches out and is delivered to the oral cavity of the user. The layer 110 of material can include a portion of the head 20 or a material layer designed to incorporate the desired criteria of release rate and dosage that is securable to the head 20. The delivery member 100 can be secured on or within at least one surface of the head 20. For example, the delivery member 100 could be secured within a groove 118 (FIG. 8) that extends along or around the head 20. Such a groove 118 could be about 1 to about 2 mm deep, relative to the outer surfaces of the head 20.

A second layer 114 is positioned over the first layer 110. This layer may be made of any material or materials that may be chemically and/or mechanically altered. Chemical and/or mechanical alteration may be accomplished by, e.g., chemical reactions initiated by components of the saliva or water, including dissolution or enzyme conversion and/or abrasion of the layer against the surfaces of die oral cavity. This layer 114 can erode due to abrasion during use of the instrument 1 or it can be formed of a water-soluble material. In an embodiment, the outer layer 114 includes a water-soluble polymer (preferably polyethylene oxide, polyethylene glycol, or polyvinyl alcohol for example). However, any known, non-toxic polymer, copolymer or combinations of the same providing a controllable water solubility to the layer can be used. The solubility of the polymer used in the outer layer 114 should be low enough that it dissolves out slowly, over a period of many uses. The second layer 114 can also include one or more oral care agents, such as an anti-microbial agent. The anti-microbial agent can be any of those discussed above, such as chlorhexidine.

Non-limiting examples of anti-microbial agents that can be used in place of chlorhexidine digluconate include antibiotics such as actinobolin, chlortetracycline, tetracycline, streptomycin, kanamycin neomycin, niddamycin, bacitracin, erythromycin, penicillin, rancemycin, gramicidin, saramycin, and polymyxin B; as well as antiplaque enzymes such as mucinases, pancreatin, fungal enzymes, protease-amylase, dextranase, moimnase, zendium, amyloglucosidase, and glucose oxidase. Other conventional antimicrobials that can be used include phenolic compounds (e.g., phenol, thymol, 2-phenylphenol, hexylresorcinol), and listerine (thymol, eucalyptol, menthol, methylsalicylate); bi-pyridines (e.g., octenidene); pyrimidines (e.g., hexetidine); halogens (e.g., iodophores, fluorides); quaternary ammonium salts (e.g., cetylpyridinium chloride, benzethonium chloride, domiphen bromide); oxygenating agents (e.g., peroxides; perborate); herbal extracts (e.g., sangnimarine); heavy metal salts (e.g., silver, mercury, zinc, copper, tin); and other bis-biguanidines besides chlorhexidine alexidine). Of course, other chlorhexidine salts like the diacetate and dihydrochloride can be used in place of chlorhexidine digluconate.

The two layers 110, 114 can be produced either by conventional co-extrusion or co-injection molding techniques, from two different mixtures. Alternatively one layer can be extruded and then the other layer can be thermoformed/compression molded or laminated onto the extruded layer. Other methods of manufacture are also contemplated.

Figure 9:
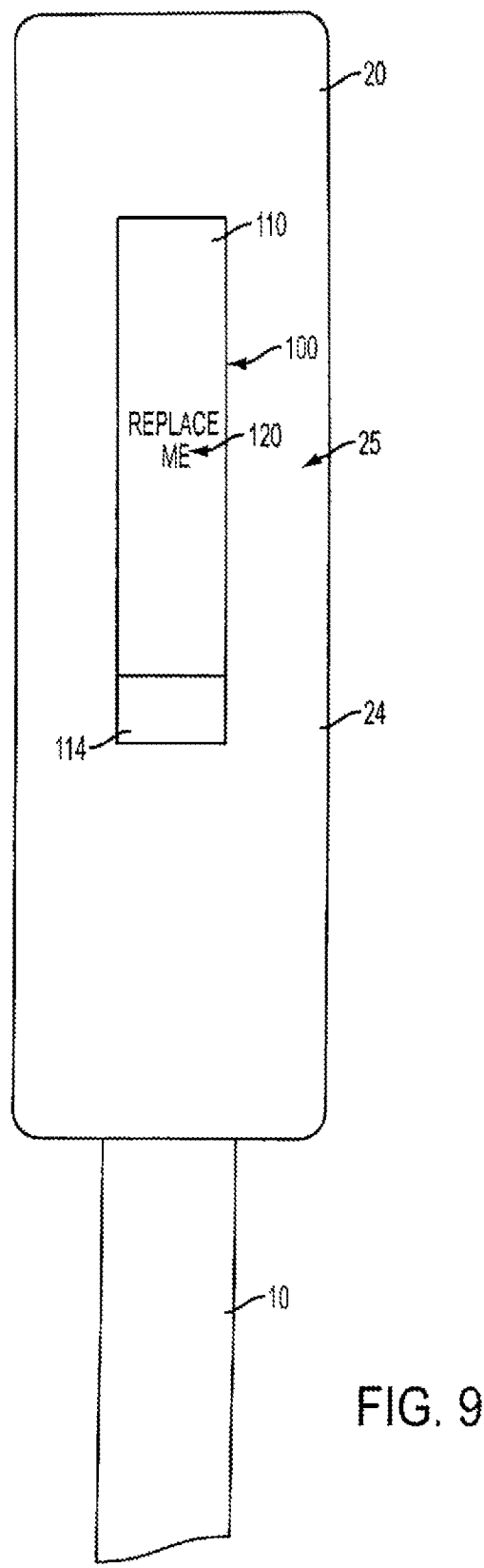
FIG. 9 illustrates an embodiment of the instrument of FIG. 2.

As the delivery member 100 comes into contact with water, saliva or a chemical in the mouth, the outer layer 114 dissolves and the oral care agent(s) leach out from the area exposed by the dissolved outer layer 114. As the outer layer 114 dissolves away with repeated use, it not only exposes the oral care agent held in the resin, for example, but it also exposes indicia 120 that indicates the wear of the instrument 1, including when the oral care agent(s) within the instrument is depleted and needs to be replaced or recharged (FIG. 9). The indicia 120 can be a visible color that attracts the user's attention to the layer 110 and illustrates that the amount of effective life remaining in the instrument 1. Alternatively, the indicia 120 can be a message that tells the user when the oral care instrument 1 is depleted (FIG. 9). Other manners of communication are also contemplated.

In an alternative embodiment, a hydrogel is applied over at least one surface of the instrument 1 and/or forms at least one layer of the delivery member 100, in this embodiment, the hydrogel releases oral care agents and/or absorbs other agents, bacteria and/or chemicals within the mouth and on the instrument 1.

Figure 10:
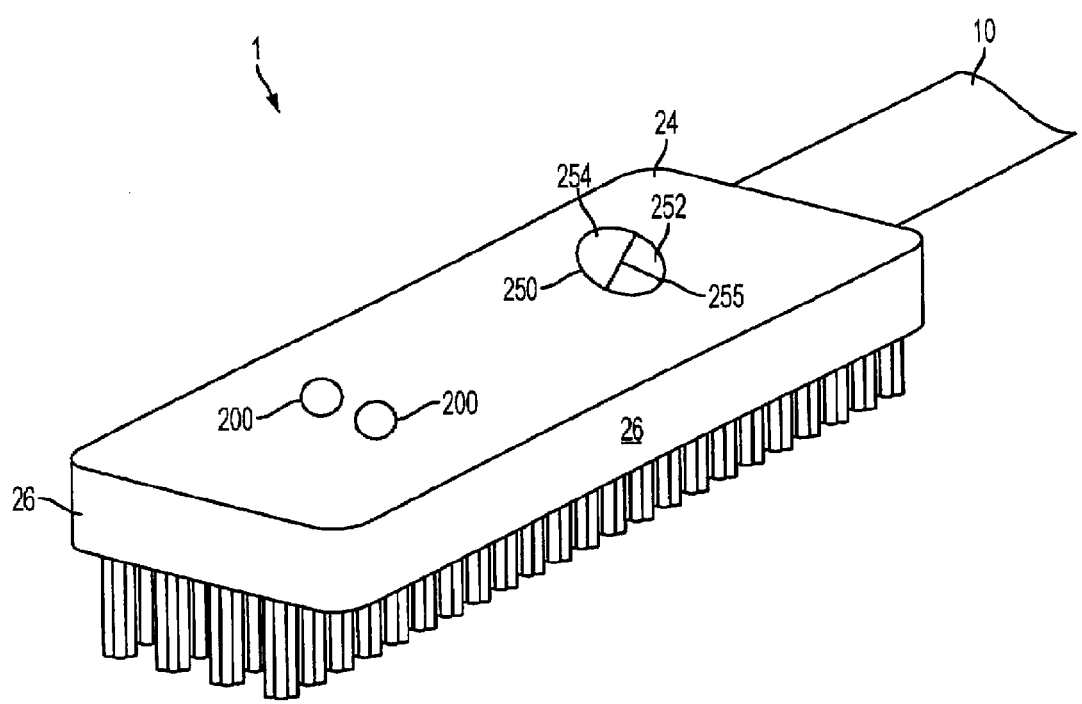
FIG. 10 is a perspective view of an alternative embodiment of an instrument according to the present invention.

In an alternative embodiment illustrated in FIG. 10, the instrument 1 can include any number of containers or capsules 200 secured to a surface of the head 20 or included within the head 20. Each capsule 200 can be formed of a biocompatible material and comprise at least one oral care agent, such as liquid and/or powder oral care agents. In certain instances, the agents provided in the capsules should not be mixed until within the mouth. These capsules 200 can burst under pressure or dissolve and release the oral care agent(s) into the oral cavity.

In another embodiment, a single container or capsule 250 having two or more chambers 252, 254 is secured to a surface of the instrument 1. In this embodiment, a membrane or barrier 255 extends between the chambers 252, 254. Over time, the membrane 255 will dissolve or break. This failure of the membrane can be time dependent and/or as a result of use of the instrument within the mouth. When the membrane 255 dissolves, breaks or otherwise wears away from an inner wall of the capsule 250, the materials in the chambers 252, 254 contact each other and cause a perceptible change that indicates that the oral care agent in the instrument 1 may be depleted.

As described above, a wide variety of molding techniques may be used in accordance with the oral care instrument, and a wide variety of material specifications and parameters may be used to provide instruments having a variety of desired characteristics. While the shapes of various preferred inventive articles are described above, it is readily understood that a wide variety of alternate shapes and sizes are contemplated by the invention. Preferably, shapes and sizes are selected such that fluid contact with the porous portion of the oral care instrument is optimized. Further, those skilled in the art will appreciate that there are numerous variations and permutations of the above described systems and techniques. It is to be understood that other embodiments may be utilized and structural and functional modifications may be made without departing from the scope of the present invention.

What is claimed is:
1. An oral care instrument comprising:
a head, at least a portion of the head including at least one oral care agent;
a wear indicator secured to a surface of the oral care instrument, the wear indicator comprising a first chamber containing a first material and a second chamber containing a second material;
a membrane positioned between the first chamber and the second chamber to separate the first material from the second material; and
wherein upon the membrane being removed, the first material contacts the second material and causes a perceptible change that indicates that the oral care agent is depleted.

2. The oral care instrument of claim 1 wherein the membrane is removed by dissolving over time during use of the oral care instrument.

3. The oral care instrument of claim 1 wherein the oral care agent is stored within a capsule that is located on the head.

4. The oral care instrument of claim 3 wherein the capsule bursts under pressure to release the oral care agent into an oral cavity.

5. The oral care instrument of claim 3 wherein the capsule dissolves over time to release the oral care agent into an oral cavity.

6. The oral care instrument of claim 1 further comprising a cavity formed into a surface of the head, wherein the at least one oral care agent is located within the cavity.

7. The oral care instrument of claim 6 wherein a first oral care agent and a second oral care agent are located within the cavity.

8. The oral care instrument of claim 7 wherein the first oral care agent is layered on top of the second oral care agent for controlled release timing.

9. The oral care instrument of claim 7 wherein the first oral care agent and the second oral care agent are different and wherein the first oral care agent is located within the cavity adjacent to the second oral care agent so that the first and second oral care agents react simultaneously upon coming into contact with an activator.

10. An oral care instrument comprising:
a head, at least a portion of the head including at least one oral care agent;
a capsule secured to a surface of the oral care instrument, the capsule comprising a first chamber containing a first material and a second chamber containing a second material, the first and second materials separated from one another by a barrier; and
wherein the barrier breaks down after a pre-determined period, of time of use of the oral care instrument so that the first and second materials contact one another and cause a perceptible change that indicates that the oral care agent is depleted.

11. The oral care implement of claim 10 wherein the barrier dissolves over time during use of the oral care instrument.

12. An oral care instrument comprising:
a head, at least a portion of the head including at least one oral care agent;
a wear indicator; and
a rupturable element on at least one surface of the oral care instrument, the rupturable element comprising the at least one oral care agent;
wherein the wear indicator comprises a first layer and a second layer that is chemically or mechanically altered over a period of many uses of the oral care instrument to expose the first layer; and
wherein the first and second layers are secured within a groove that extends around the head.

13. The oral care instrument of claim 12, wherein the second layer includes a material having cavities that comprise a second oral care agent.

14. The oral care instrument of claim 12, wherein exposure of the first layer upon chemical or mechanical altering of the second layer indicates when the oral care instrument should be discarded or recharged with additional oral care agents.

15. The oral care instrument of claim 12, wherein at least one of the layers includes an oral care agent.

16. The oral care instrument of claim 12, wherein the wear indicator visually communicates the existence of the at least one oral care agent.

17. The oral care instrument of claim 12, wherein the wear indicator comprises a plurality of different materials that, when in contact, cause a perceptible change that indicates that the at least one oral care agent is depleted.

18. An oral care instrument comprising:
- a head, at least a portion of the head including at least one oral care agent;
- a wear indicator;
- a rupturable element on at least one surface of the oral care instrument, the rupturable element comprising the at least one oral care agent;
- wherein the wear indicator comprises a plurality of different materials that when in contact, cause a perceptible change that indicates that the at least one oral care aunt is depleted; and
- a membrane positioned between the plurality of different materials, the membrane wearing away during use of the oral care instrument to allow the plurality of different materials to contact.

* * * * *